(12) United States Patent
Ivanov et al.

(10) Patent No.: US 7,718,154 B2
(45) Date of Patent: *May 18, 2010

(54) PROCESS FOR PRODUCING BORANES

(75) Inventors: Sergei Vladimirovich Ivanov, Schnecksville, PA (US); Baldomero Casas, Emmaus, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/448,006

(22) Filed: Jun. 7, 2006

(65) Prior Publication Data

US 2006/0286019 A1    Dec. 21, 2006

Related U.S. Application Data

(60) Provisional application No. 60/691,221, filed on Jun. 16, 2005.

(51) Int. Cl.
C01B 35/00 (2006.01)
C01B 35/10 (2006.01)
C01B 35/14 (2006.01)
C01B 6/13 (2006.01)

(52) U.S. Cl. ............... 423/294; 423/276; 423/284; 423/286; 423/288; 423/283

(58) Field of Classification Search ......... 423/288, 423/277, 286, 276, 279, 280, 283, 284, 294; 455/188.1, 132, 266, 313, 314, 318, 323, 455/324; 375/324, 340, 343
See application file for complete search history.

(56) References Cited

U.S. PATENT DOCUMENTS 2,830,070 A * 4/1958 Cunningham ......... 558/296
2,927,124 A    3/1960 Bache et al.
2,969,274 A    1/1961 Kyllonen
3,013,016 A    12/1961 Haberland et al.
3,127,448 A    3/1964 Hinckley et al.
3,169,045 A    2/1965 Miller et al.
3,257,455 A    6/1966 Ashby
3,265,737 A    8/1966 Miller
3,328,134 A    6/1967 Miller et al.

(Continued)

FOREIGN PATENT DOCUMENTS

CN    1303386 A    7/2001

(Continued)

OTHER PUBLICATIONS

Booth, Harold Simmons; *Inorganic Syntheses*; vol. 1; McGraw-Hill Book Company, Inc. NY; 1939; pp. 21-23.

(Continued)

*Primary Examiner*—Stanley Silverman
*Assistant Examiner*—Jennifer A Smith
(74) *Attorney, Agent, or Firm*—Michael K. Boyer

(57) ABSTRACT

This idea relates to the synthesis of salts of dodecahydrododecaborate B12H12 (2-). In the proposed process a metal hydride is reacted with an alkyl borate in the presence of a Lewis base to produce Lewis base-borane compex, which is thermally decomposed to produce salts of B12H12 (2-), while alkyl borare is recovered from the reaction by-product and is recycled.

32 Claims, 1 Drawing Sheet

U.S. PATENT DOCUMENTS

| | | | | |
|---|---|---|---|---|
| 3,355,261 | A | * | 11/1967 | Miller et al. ............... 423/288 |
| 3,961,017 | A | | 6/1976 | Hough et al. |
| 5,144,032 | A | | 9/1992 | Arduengo |
| 5,886,229 | A | | 3/1999 | Bruening et al. |
| 2004/0166044 | A1 | * | 8/2004 | Ashby ....................... 423/288 |
| 2005/0053841 | A1 | | 3/2005 | Ivanov et al. |
| 2005/0064288 | A1 | | 3/2005 | Ivanov et al. |
| 2006/0286019 | A1 | * | 12/2006 | Ivanov et al. ............... 423/277 |
| 2006/0286020 | A1 | * | 12/2006 | Ivanov et al. ............... 423/277 |

FOREIGN PATENT DOCUMENTS

| | | |
|---|---|---|
| CZ | 238254 | 11/1985 |
| DE | 1792040 | 10/1971 |
| DE | 1792040 A1 | 10/1971 |
| GB | 822229 | 10/1959 |
| JP | 2006-347874 A | 12/2006 |

OTHER PUBLICATIONS

Gruner, B.; "Reaction of Sodiu Hydride of High Surface Area with Boron Trichloride;" Solid State Inorg. Chem, ISSN 0992-43612/91/3; Dec. 1990; pp. 597-607.

Sivaey, I et akl "Chemistry of closo-Dodecaborate Anion $(B_{12}H_{12})^{2-}$:A Review;" et al.; Collect. Czech. Chem. Commun. (vol. 67) (2002)—pp. 679-727.

Miller H.C et al.; Inorganic Chemistry; Central Research Dept. Experimental Station, Contribution No. 965; (vol. 3, No. 10) (1964)—pp. 1456-1463.

Miller H. C. et al: "Chemistry of boranes. XX. Syntheses of polyhedral boranes" Inorganic Chemistry, 1964, pp. 1456-1463, "Reaction of base and boron hydride"; "B12H12 Synthesis. (B) From Triethylamine and diborane".

Miller, H.C., et al; "Chemistry of Boranes. XX. Synthesis of Polyhedral Boranes"; Inorganic Chemistry, American Chemical Society; Easton, US; Jan. 1, 1964; pp. 1456-1463; XP002401791.

Sivaev, I.B., et al; "Chemistry of Closo-Dodecaborate Anion"; Collection of Czechoslovak Chemical Communications, Institute of Organic Chemistry & Biochemistry; Prague; Jan. 1, 2002; pp. 679-727; XP002391004.

Sivaev, I.B., et al; "Chemistry of Closo-Dodecaborate Anion"; Collection of Czechoslovak Chemical Communications, Institute of Organic Chemistry & Biochemistry; pp. 679-727; Jan. 1, 2002; XP002391004.

Miller, H.C., et al; "Chemistry of Boranes, XX. Syntheses of Polyhedral Boranes"; Inorganic Chemistry, American Chemical Society, Easton, US; pp. 1456-1463; Jan. 1, 1964; XP-002401791.

Gaines, D., et al; "Convenient Preparations of Solutions Containing the Triborohydride Ion"; Inorganic Chemistry; vol. 2, No. 3; 1963; pp. 526-528; XP-002483093.

Jensen, W.; "The Lewis Acid-Base Definitions: A Status Report"; Chemical Reviews: vol. 78, No. 1; 1978; pp. 1-22; XP-002483094.

Toft, M., et al; "New, Systematic Synthesis of Boron Hydrides Via Hydride Ion Abstraction Reacations: Preparation of B2H6, B4H10, B5H11 and B10H14"; Inorganic Chemistry; vol. 21; 1981; pp. 1952-1957; XP-002483276.

Ellis, I., et al; "A Convenient Preparation of B12H122-Salts"; Journal of Americal Chemical Society; pp. 526-528; 1963; XP-002508357.

Gruner, B., et al; "Reaction of Sodium Hydride of High Surface Area with Boron Trichloride"; Eur. J. Solid State Inorg. Chem.; vol. 28; 1991; pp. 597-609; XP-002509170.

Miller, H.C., et al; "Synthesis of Polyhedral Boranes"; Journal of Amierical Chemical Society; vol. 85; pp. 3885-3886; 1963; XP-002509186.

* cited by examiner

Figure 1. Process Block Diagram for Synthesis of Na2B12H12 from NaH and B(OMe)3
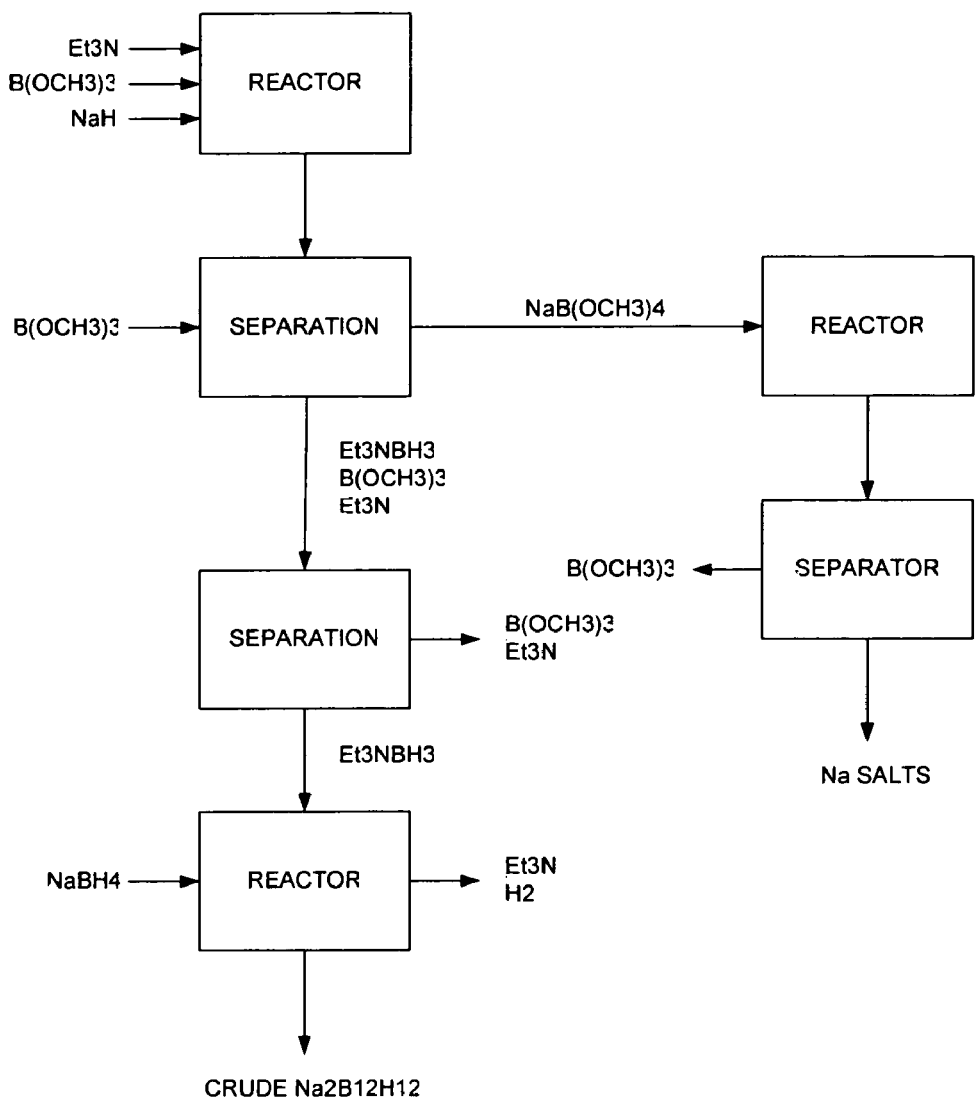

PROCESS FOR PRODUCING BORANES

CROSS-REFERENCE TO RELATED APPLICATIONS

This application claims benefit of U.S. Provisional Application No. 60/691,221, filed on Jun. 16, 2005. The disclosure of this Provisional Application is hereby incorporated by reference.

The subject matter of this application is also related to copending and commonly assigned U.S. patent application Ser. No. 11/448,021, filed on Jun. 7, 2006 herewith, and entitled "Method For Producting Dodecahydrododecaborates"; hereby incorporated by reference.

FIELD OF THE INVENTION

The instant invention relates to borane compositions and methods for making boranes, and using the boranes for making Li2B12F12 (and related compounds).

BACKGROUND OF THE INVENTION

Methods are known in this art for making certain borane compounds. Previous methods for synthesis of dodecahydrododecaborates involve reactions of diborane with metal tetrahydroborates, or pyrolysis of borane complexes.

U.S. Pat. Nos. 3,265,737, 3,169,045 and 3,328,134 disclose preparing $B_{12}H_{12}^{2-}$ by condensing diborane with tetrahydroborates in the pressure vessels: "A process for preparing alkali metal and alkaline earth metal dodecahydrododecaborates which comprises reacting a) diborane
b) a tetrahydroborate selected from the class consisting of alkali metal tetrahydroborates and alkaline earth tetrahydroborates, and
c) a compound selected from those of the formulas consisting of RO(CH2CH2O)R', R'SR', RR'R" N and RR'R" P . . . at a temperature of at least 120C in the substantial absence of oxygen and water and a pressure of about one atmosphere"

Another group of methods comprise reacting various boranes with L.BH3 complexes. For example, U.S. Pat. No. 3,961,017 describes a process for the synthesis of $Na_2B_{12}H_{12}$ using diborane adduct, dimethylsulfideborane: "A process for preparing an alkali metal dodecahydrododecaborate which comprises reacting . . . alkali metal hydride with dimethylsulfideborane . . . ". Czech Patent No. 238254 provides a process based on thermal decomposition of borane-triethylamine complex in the presence of metal tetrahydroborates: "A process for preparing an alkali metal dodecahydrododecaborate which comprises reacting . . . alkali metal hydride with triethylamine borane at 220-250 C. . . ."

Other methods are disclosed in Miller, H. C.; Muetterties, E. L. U.S. Pat. No. 3,555,261; Ashby, E. C. U.S. Pat. No. 3,257,455; Sivaev, I. B.; Bregadze, V. I.; Sjoberg, S. Collect. Czech. Chem. Commun., 2002, 679; Miller, H. C.; Miller, N. E.; Muetterties, E. L. Inorganic Chemistry, 1964, 1456; Kyllonen, D. M. U.S. Pat. No. 2,969,274, 1961

The disclosure of all of the previously identified references is hereby incorporated by reference. Such incorporation shall not be an admission that these references are prior art against any claims appended hereto.

BRIEF SUMMARY OF THE INVENTION

The instant invention solves problems associated with conventional methods by providing a cost effective process for producing salts of B12H12$^{2-}$. The instant invention also solves problems with conventional methods by employing a process that is substantially free of diborane. By "substantially free" of diboranes it is meant that the reactants, isolated intermediates and products contain less than about 5 mol. % diborane (when measured in a gaseous phase) and normally less than about 1 mol. % diborane. The instant invention provides a process for producing dodecahydrododecaborate salts from commercially available materials, such as metal hydrides (e.g., sodium hydride), and alkyl borates (e.g., trimethylborate).

The inventive methods can produce borane containing compositions that can be used for making B12FxY12-x$^{2-}$ including, without limitation, Li2B12FxY12-x, where Y can be any combination of atoms or functional groups including, without limitation, hydrogen, chlorine, other halogens and OR groups, and any salts or precursors thereof and combinations containing LBF containing compositions (collectively referred to as "LBF"). For example, $B_{12}H_{12}^{2-}$ salts can be used for making $Li_2B_{12}Cl_{12}$ and Li2B12F12-xHx. The LBF can be employed as a source of lithium in lithium batteries. Examples of methods for using the inventive borane compositions to produce LBF are disclosed in U.S. Patent Application Nos. US20050053841 A1 and US20050064288 A1; hereby incorporated by reference.

The instant invention relates to methods for producing salts of dodecahydrododecaborate, $B_{12}H_{12}^{2-}$. The instant invention provides a process for producing dodecahydrododecaborate salts (2-) from commercially available materials, such as metal hydrides (e.g., sodium hydride), and alkyl borates (e.g., trimethylborate).

In one aspect of the present invention, at least one metal hydride is reacted with at least one alkyl borate, $B(OR)_3$ in the presence of at least one Lewis base to form a Lewis base-borane complex, L.BH3 and a reaction by-product, metal salt comprising at least one alkylborate. Lewis base-borane complex is separated from the reaction by-product and is heated (e.g., at a temperature of about 120 to about 250° C.), with a metal salt, MX, to form dodecahydrododecaborate salts. Normally alkyl borate is recovered from the by-product and a recycled.

BRIEF DECRIPTION OF THE DRAWINGS

FIG. 1 is a block diagram of a process according to one aspect of the invention.

DETAILED DESCRIPTION OF THE INVENTION

The present invention relates to a process for producing dodecahydrododecaborate salts, wherein at least one metal hydride is reacted with at least one alkyl borate B(OR)3 in the presence of at least one Lewis base to form at least one Lewis base-borane compex, L·BH3. A reaction by-product comprising a metal salt of tetraalkylborate, MB(OR)$_4^-$ or its mixture with metal alkoxide, M(OR)x (x is 1, 2, 3) can also be formed. The Lewis base-borane complex can be separated by filtration, distillation, decantation, centrifugation or any other well known in the art technique for separation of liquid and solid, from the reaction by-product, and is heated at a temperature of about 120 to about 250° C. neat or in an inert solvent, such as hydrocarbon solvent or ether type solvent with at least one metal salt MX, where M is a metal cation and X is an anion, to form metal dodecahydrododecaborate salts. The alkyl borate can be recovered from the by-product and recycled.

When metal hydride comprises alkali metal hydride, MH, 1.33 equiv. of alkyl borate are reacted with one equiv. of metal hydride. However, to improve the reaction yield, alkyl borate to metal hydride ratio may vary from 1 to 100 depending on the reaction conditions, such as temperature, solvent, agitation, among other process parameters. The ratio of metal hydride and Lewis base is between 0.1 and 3, usually between 1 and 3. When metal hydride comprises an alkali metal hydride, MH, one equivalent of reaction by-product MB(OR)4 is formed per one equivalent of metal hydride added. When metal hydride comprises a mixed metal hydride, such as, for example sodium aluminum hydride, approximately one equivalent of trialkoxy aluminate Al(OR)3 and one equivalent of NaB(OMe)4 are formed. The ratio between L·BH3 and the salt MX is maintained to correspond to the metal and boron ratio in the starting mixture and in the desired product metal salt of dodecahydroborate, $M_2(B12H12^-)n$, wherein n is metal valence and n is 1,2, 3.

Amine-borane produced according to the method described in this invention can be used for the synthesis of salts of dodecahydrododecaborate or for other applications, such as in reductive amination reactions, in hydroboration of alkenes and alkynes, in electroless plating of metals and for other applications. The salts of dodecahydrodecaborate can be used for making LBF such as described in U.S. Patent Application No. US20050053841A1 and US20050064288 A1; previously incorporated by reference.

While any suitable alkyl borate can be recovered, typical examples of the alkyl borates, $B(OR)_3$, comprise at least one member from the group consisting of trimethyl borate, tryethyl borate, triisopropyl borate, triphenyl borate and combinations thereof. A desirable alkyl borate comprises trimethyl borate, $B(OMe)_3$, where Me is methyl, $CH_3$.

While any suitable metal hydride can be employed in the inventive process, typical examples of metal hydrides used in this invention comprise at least one member from the group consisting of sodium hydride, NaH, potassium hydride, KH, magnesium hydride, MgH2, calcium hydride, CaH2, sodium aluminum hydride, NaAlH4, and lithiumaluminum hydride, LiAlH4, and mixtures thereof. Sodium hydride is a desirable metal hydride used in this invention due to low cost and commercial availability.

Typical examples of Lewis bases used in this invention comprise amines having a general formula R'R"R'"N, alkyl sulfides of general formula R'SR" and phospines of general formula RR'R"P. Lewis bases are chosen from those that form relatively stable complexes with borane and do not react significantly with the reaction by-products under reaction conditions, and can be separated from the reaction by-products and converted to the salts of dodecahydrododecaborate under thermal treatment. While any suitable Lewis base can be employed, one such base comprises amines such as aliphatic and aromatic amines While any suitable metal salt can be employed, typical examples of metal salts MX used in thermal condensation of Lewis base-borane complexes comprise metal hydrides, where X comprises hydride H—, metal tetrahydroborates, where X comprises tetrahydroborate anion BH4-, metal alkoxides, where X comprises an alkoxide, OR— and metal tetraalkylborates, where X comprises tetraalkylborate anion, B(OR)4-, or a mixture of those Tetrahydroborates and tetraalkylborates are desirable MX compositions. Typical examples of metal cations M used in the described compositions comprise alkali, alkali earth metals and aluminum. Alkali metals are desirable with sodium cation being useful.

Certain aspects of the instant invention are illustrated by FIG. 1 which is a block diagram of a process wherein salts of dodecahydroborate anion are produced by reactions among sodium hydride, NaH, trimethylborate, $B(OCH_3)_3$ (TMB) and triethylamine, $N(C2H5)3$ (TEA). Referring now to FIG. 1, a process using the following reactions is shown:

(step 1)

The reaction by-product in step 1 is recycled according to the one of the following processes

(step 2)

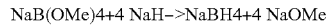

Borane triethylamine borane can be converted to Na2B12H12 according to one of the following reactions:

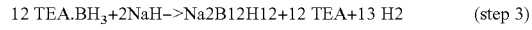

(step 3)

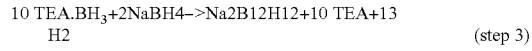

(step 3)

Overall reaction for the described process is:

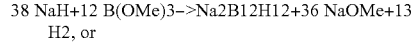

when using sulfuric acid to recycle trimethyl borate:

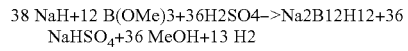

The first step of the process illustrated in FIG. 1 comprises generating a borane-amine complex from sodium hydride and trimethyl borate. The ratio of trimethyl borate to metal hydride is between 1 and 100, usually between 1 and 10, and normally between 1 and 5. Concentration of sodium hydride in the reaction mixture is between 0.1 to 10 wt %, usually between 1 and 5 wt %. Sodium hydride is used as commercially available 60 wt. % dispersion in oil or it can be used as 1 to 60% dispersion in one of the above solvents. The temperature range for this reaction is about −20 to about 100° C. The reaction can be conducted in the excess of one of the liquid reagents, such as TEA or TMB, or in at least one inert solvent, such as hydrocarbon solvents, or in ether type solvent. When the reaction is conducted in the hydrocarbon solvent or in the excess of TEA or TMB, some of the reaction intermediates, such as NaBH(OMe)3 and the reaction by-product, NaB(OMe)4, are insoluble and may deposit on the surface of sodium hydride. When ether solvents, such as diethyl ether, glymes and tetrahydrofuran are used, the reaction by-product and/or reaction intermediates are soluble and the reaction proceeds relatively fast and with effective yields at about 25° C. Typically the temperature range for this reaction ranges from about −20 to about 50° C. Tetrahydrofuran is a useful solvent because all reaction products are at least partially soluble in this solvent.

When the reaction between NaH, TMB and TEA is conducted in hydrocarbon solvents concentration of NaH can be between 0.1 and 10 wt %, concentration of TMB is between 1 and 90 wt %, and concentration of TEA is between 1 and 90 wt %. In this case the reaction by-product is typically insoluble and is separated by filtration, centrifugation or decantation. TEA, TMB and amine-borane are separated by distillation. Typically TEA and TMB are distilled below 100° C. (bp of TEA is 88.8° C. and bp of TMB is 68° C.). Amine borane can be distilled off under reduced pressure 0.01 to 500 torr below 100° C. to prevent its reaction with the reaction by-product NaB(OMe)4. TEA and TMB are recycled, while amine-borane may be used for production of dodecahydrododecaborate.

When the reaction between NaH, TMB and TEA is conducted in tetrahydrofuran a homogeneous solution is formed. Concentration of the reaction by-product NaB(OMe)4 in the reaction solution is usually maintained below 50 wt %. Typically NaH to TMB molar ratio is between 1 and 5, and sodium hydride to triethylamine molar ratio is between 0.3 and 2. Tetrahydrofuran, TMB, TEA and amine-borane are distilled under reduced pressure below about 100° C. to prevent reaction of amine-borane with the reaction by-product, NaB(OMe)4. Any solid by-product is dried, washed with solvent and TMB is recovered according to the procedures described below.

In the second step of the process illustrated in FIG. 1, TMB is recycled from the reaction by-product, NaB(OMe)4. If complex hydrides are used to generate Lewis base borane complex, then the by-product may also contain a mixture of metal akoxides. For example, when metal hydride comprises sodium aluminum hydride, the by-product of the reaction can comprise a mixture of sodium tetraalkylborate, NaB(OR)4, aluminum alkoxide Al(OR)3 and sodium aluminum alcoxide NaAl(OR)4.

In one aspect of the second step, TMB is recovered from NaB(OMe)$_4$ by treating with concentrated sulfuric acid according to the following reaction:

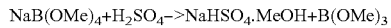
NaB(OMe)4+H2SO4->NaHSO4.MeOH+B(OMe)3

In this aspect solid NaB(OMe)$_4$ is mixed with an inert dispersant or dissolved in a solvent and the mixture is treated with concentrated sulfuric acid at temperature ranging from about −20 to about 80° C. In this case a solid product comprising sodium bisulfate can be formed, while evolved TMB remains in the liquid fraction and is distilled off or decanted away from the sodium bisulfate. Hydrocarbon solvents, TMB or TMB/methanol mixture can also be used to disperse NaB(OMe)4. Concentration of NaB(OMe)4 in the solvent is typically between 5 and 50 wt %. TMB or TMB/methanol mixtures are useful as solvents.

In another aspect of the second step, TMB is recovered from NaB(OMe)$_4$ by thermal treatment of NaB(OMe)$_4$ at a temperature of about 150 to about 350° C. according to the following reaction:

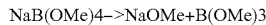
NaB(OMe)4->NaOMe+B(OMe)3

In a further aspect of the second step, TMB is used for converting NaB(OMe)4 to NaBH4 according to the following reaction:

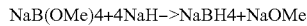
NaB(OMe)4+4NaH->NaBH4+NaOMe

Sodium borohydride produced by this process can be used for the synthesis of salts of dodecahydroborate (and, if desired, into LBF), or for other applications.

In the third step illustrated in FIG. 1, salts of dodecahydroborate are produced by thermal condensation of Lewis base borane complexes. In one aspect of the third step, Lewis base borane complexes are heated in the presence of at least one metal salt, such as metal hydride, metal alkoxide, metal tetrahydroborate, and metal tetraalkylborate. The ratio between Lewis base borane complex and metal salt can vary depending upon the quantities of dodecahydrododecaborate anion desired. In order to increase yields, the ratio between L·BH3 and salt is maintained to correspond to the metal and boron ratio in the starting mixture and in the desired product metal salt of dodecahydroborate, $M^2(B_{12}H_{12})_n$, wherein n is metal valence. For example, if the metal salt comprises sodium hydride a useful ratio between Lewis base borane complex and sodium hydride is 12 to 2 according to the reaction:

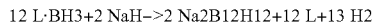
12 L·BH3+2 NaH->2 Na2B12H12+12 L+13 H2

In another example, if metal salt comprises sodium tetrahydroborate a desirable ratio between Lewis base and sodium tetrahydroborate is 10 to 2 according to the following reaction:

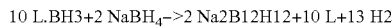
10 L·BH3+2 NaBH4->2 Na2B12H12+10 L+13 H2

Amines are useful as Lewis bases in the instant invention. While any suitable amine can be used, examples of such amines comprise at least one of triethylamine, tripropyylamine, N-ethylmorpholine, diethylaniline, and combinations thereof. The condensation reaction between a Lewis base borane complex and metal salt can be conducted in inert solvents, such as hydrocarbon solvents or glymes, or it can be conducted in neat Lewis base borane complexes. If neat liquid Lewis base borane complex is used, initial concentration of metal salt in the neat Lewis base borane complex is typically between 1 wt % and 25 wt %. If inert solvent is used, concentration of Lewis base borane in the solvent is normally between 1 wt % and 99 wt %. The reaction is normally conducted under pressure 1 atm or above and in the temperature range of about 150 to about 250 C (e.g., about 180 to about 220° C.).

If desired, at least one Lewis base, which is generated during thermal condensation of Lewis base borane complex to form salts of dodecahydroborate anion, can be recycled to the process for generating Lewis base borane complex.

The following Examples are provided to illustrate certain aspects of the invention and shall not limit the scope of any claims appended hereto.

EXAMPLES

Example 1

This example demonstrates a process for synthesis of amine borane complex from sodium hydride, trimethylborate and triethylamine in hexadodecane, and separation of the reaction by-product, sodium tetramethoxyborate, by filtration.

A solution of triethylamine (4.5 ml) and trimethylborate (7.5 ml) in hexadodecane (8 ml) was treated with 1.05 g of sodium hydride (60% dispersion in mineral oil) at 65° C. under nitrogen atmosphere in a 50 ml flask for 2 hours. The resultant solid was separated from the liquid by filtration in a fritted disk separatory funnel. 11 B NMR of the liquid fraction revealed a new quartet at −12.5 ppm, which upon 1H decoupling was converted to a singlet and was identified as borane triethylamine, Et3NBH3. The liquid fraction was heated to 100° C. in a 50 ml flask, and excess of triethylamine and trimethylborate were distilled off. Borane triethylamine was distilled under 0.01 torr vacuum at 70° C. and was also identified by IR spectroscopy (v (B—H) is 2279, 2327 and 2383 cm-1).

Example 2

This example demonstrates a process synthesis of amine borane complex from sodium hydride, trimethylborate and triethylamine in triglyme, and separation of the reaction by-product, sodium tetramethoxyborate, by centrifugation.

Sodium hydride (0.77 g of 60 wt % suspension in oil) was added using solids additional funnel to the solution of triethylamine (5.0 ml) and trimethylborate (7.5 ml) in triglyme (7.5 ml) in a 50 ml flask at 25° C. under nitrogen atmosphere. During the addition an increase in the reaction temperature was observed thereby indicating an exothermic reaction and a large amount of solid was formed. The mixture was diluted with 20 ml of toluene and centrifuged off. The liquid portion was decanted out and analyzed by 11B and 1H NMR. The analysis detected a mixture comprising unreacted trimethylborate (11B NMR, 18.77 ppm, Int.=1) and the reaction products borane-triethylamine ($^{11}$B NMR, −12.5 ppm, Int.=0.32, 64% conversion based on NaH) and sodium tetramethoxyborate, NaB(OMe)4. The solid was dried under 0.01 torr vacuum and 4.3 g of solid NaB(OMe)$_4$ was collected (86% yield based on NaH).

Example 3

This example demonstrates a process for generating amine borane complex from sodium hydride, trimethylborate and triethylamine in triethylamine.

Sodium hydride (1.4 g of 60 wt. % dispersion in mineral oil) was added via solids additional funnel to the solution of triethylamine (15.0 ml) and trimethylborate (7.5 ml) in a 50 ml 3 neck flask at 25° C. under nitrogen atmosphere. The reaction mixture was agitated at 25 C for 24 hours. During the reaction a relatively large amount of solid was formed. A sample of the mixture was diluted with triethylamine and analyzed by $^{11}$B NMR. Based on the integration of $^{11}$B NMR signals of unreacted trimethylborate (11B NMR, 18.77 ppm, Int.=1) and the reaction product borane-triethylamine ($^{11}$B NMR, −12.5 ppm, Int.=0.1), the conversion of trimethylborate to borane-triethylamine was ~30 mol %. Borane-triethylamine, trimethylborate and triethylamine were separated by distillation.

Example 4

This example demonstrates a process for generating amine borane complex from sodium hydride, trimethylborate and triethylamine in tetrahydrofuran. This process provides the advantage of all the reaction products being soluble and the reaction being effective at about 25° C.

In a 50 ml flask under nitrogen atmosphere a solution of trimethylborate (6.5 g) and triethylamine (2.8 g) in tetrahydrofuran (8.7 g) was treated over 1.5 h at 25-40° C. with the suspension of NaH (1.74 g of 60% dispersion in oil) in tetrahydrofuran (9.3 g). The reaction was highly exothermic and NaH was added by small portions. An increase in the reaction temperature was observed and NaH was completely dissolved within ~2-3 minutes. According to 11B NMR of the reaction solution, trimethylborate converted to a mixture of sodium tetramethylborate, NaB(OMe)$_4$ (11B NMR, 2.57 ppm, Int.=1) and borane-triethylamine (11B NMR, −12.5 ppm, Int.=0.26) with >87% yield. The reaction solution was heated under nitrogen atmosphere and most of THF, triethylamine and residual trimethylborate were distilled out. The mixture was placed under vacuum and a liquid with freezing point around 0° C. was distilled out under vacuum and identified by $^{11}$B NMR as a mixture of borane-triethylamine and dimethoxyborane-triethylamine. The solid residue was analyzed as a mixture of NaB(OMe)4 (89 mol %), borane-triethylamine (6 mol %) and sodium borohydride (5 mol %).

Example 5

This example demonstrates a process for generating amine borane complex from sodium hydride, trimethylborate and triethylamine in tetrahydrofuran with recovery of trimethyl borate.

In a 50 ml flask under nitrogen atmosphere a solution of trimethylborate (6.5 g) and triethylamine (2.8 g) in tetrahydrofuran (8.7 g) was treated over 1.5 h at 25-40° C. with the suspension of NaH (1.74 g of 60% dispersion in oil) in tetrahydrofuran (9.3 g). The reaction was highly exothermic and NaH was added by small portions. An increase in the reaction temperature was observed and NaH was completely dissolved within ~2-3 minutes. According to $^{11}$B NMR of the reaction solution, trimethylborate was converted to a mixture of sodium tetramethylborate, NaB(OMe)$_4$ and borane-triethylamine with >87% yield. The clear solution was purged overhead with carbon dioxide and a large amount of solid was formed. The solid was filtered, dried and 2.2 g of solid was collected. The amount of tetramethylborate in the solution was reduced compare to its amount before carbon dioxide treatment.

Example 6

This example demonstrates the process for generation of amine borane complex from sodium aluminum hydride, trimethylborate and triethylamine in tetrahydrofuran.

In a 50 ml flask under nitrogen atmosphere a solution of trimethylborate (2.4 g) and triethylamine (1.4 g) in tetrahydrofuran (7 ml) was treated with a suspension of NaAlH$_4$ (0.5 g) in tetrahydrofuran (5 ml) at 25° C. for 0.5 hour. According to 11B NMR, the suspension was formed containing Et$_3$NBH$_3$, NaAl(OMe)$_4$ and NaB(OMe)$_4$:

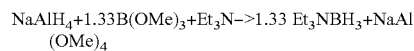

In the case of large excess of B(OMe)$_3$ the formation of NaB(OMe)$_4$ is also possible:

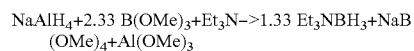

Example 7

This example demonstrates the process for recovery of trimethylborate from the reaction by-product sodium tetramethylborate, NaB(OMe)$_4$.

3.6 g of crude sodium tetraalkylborate, NaB(OMe)$_4$ was isolated by the filtration from the reaction between trimethyl borate, sodium hydride and triethylamine in hexadodecane. In a 25 ml flask under nitrogen atmosphere the solid was suspended in 7 ml of trimethylborate and treated with 1.0 g of methanol. To this solution concentrated sulfuric acid (2.0 g) was added at 0° C. via a syringe. A mixture of a solid and a liquid was formed. The liquid portion of the mixture was decanted out and identified by 11B and 1H NMR as a mixture of trimethyl borate and mineral oil. Methanol was not present in the liquid phase according to 1H NMR of the spectrum. This trimethylborate solution can be recycled back for generation of amine borane complex form sodioum hydride and trimethylborate without further purification. The solid was dried under vacuum and 1.6 g of dry powder was collected, which was identified as NaHSO4.0.5 H2SO4.0.3 MeOH.

Example 8

This example demonstrates the process for synthesis of sodium dodecahydrododecaborate, Na2B12H12, from diethylaniline borane and sodium borohydride in triglyme.

A solution of 1 ml of diethylaniline borane in 5 ml of triglyme was treated with 0.06 g of sodium borohydride at 25 C. This solution was heated at 160° C. under nitrogen atmosphere for 1 hour. The formation of white solid was observed.

The mixture was cooled to 25 C, filtered and solid was redissolved in water to obtain the solution of sodium dodecahydrododecaborate, Na2B12H12 (11B NMR, −15.9 ppm)

Example 9

This example demonstrates the process for synthesis of triethylammonium salt of dodecahydrododecaborate, [Et3NH]2B12H12, from triethylamine borane and sodium borohydride.

In a 250 ml flask equipped with a thermocouple, condenser, and nitrogen purge tube borane triethylamine (75 ml, 58.7 g, 511.5 mmol,) was added to NaBH4 (2.2 g, 58.2 mmol, powder) at 25° C. under nitrogen atmosphere. The temperature of the reaction mixture was raised to 190° C. within ~30-40 minutes. At this time evolution of hydrogen and condensation of triethylamine in the condenser was observed. After 1.5 hours 35.3 g of Et3N was collected from the distillate (349.5 mmol, 68.3% yield based on Et3NBH3). The reaction was cooled down to 50° C. and residual borane triethylamine was removed under vacuum. The solid was dried under 0.01 torr vacuum at 100° C. for 1 hour and 12.4 g of Et3NBH3 were collected from condensate (108.0 mmol, 21 mol %). The product (dry solid) was treated with 50 ml of 1% NaOH and two layers mixture is formed. The mixture was centrifuged, separated on the separatory funnel and Et3NBH3 (3.4 g, 29.6 mmol, 5.7 mol %) was collected from the top layer. Aqueous fraction was transferred into 100 ml beaker and neutralized with 1 M HCl to pH=5 and treated with 40% aqueous solution of Et3NHCl (8.0 g). The precipitate (~95% purity) was collected by filtration using fritted disk funnel and dried under vacuum to obtain 7.8 g of (Et3NH)2B12H12 (77.5% yield based on NaBH4, ~65% yield based on reacted Et3NBH3).

Example 10

This example demonstrates the process for synthesis of sodium salt of dodecahydrododecaborate, Na2B12H12, from triethylamine borane Et3NBH3, and sodium tetraalkylborate, NaB(OMe)4.

2.4 g of crude sodium tetraalkylborate, isolated from the reaction between sodium hydride, trimethylborate and triethylamine (step 1 in the invented process), were mixed with 10 ml of borane triethylamine in 50 ml flask and the mixture was heated at 220° C. (oil bath temperature) for 2.5 hours to form a paste-like solid. The mixture was cooled to 25° C. and the solid was dissolved in 5% sodium hydroxide. Based on $^{11}$B NMR of the solution Na2B12H12 (11 B NMR, −15.9 ppm) was obtained with ~80% yield.

Example 11

This example demonstrates the process for synthesis of sodium salt of dodecahydrododecaborate, Na2B12H12, from N-ethylmorpholine-borane and sodium tetrahydroborate.

In a 25 ml test tube under nitrogen atmosphere 0.23 g of sodium tetrahydroborate were suspended in 4.0 g of N-ethylmorpholine borane. The mixture was heated at 230° C. (oil bath temperature) for 10 min and 0.9 g of liquid was distilled out. The mixture was cooled to 25° C. and the solid was extracted into 10 ml of 5% NaOH. A mixture of Na2B12H12 (64 mol %) and Na2B10H10 (36 mol %) was obtained.

Although certain aspects of the invention are illustrated and described herein with reference to given embodiments, it is not intended that the appended claims be limited to the details shown. Rather, it is expected that various modifications may be made in these details by those skilled in the art, which modifications may still be within the spirit and scope of the claimed subject matter and it is intended that these claims be construed accordingly.

The invention claimed is:

1. A process for producing salts of dodecahydrododecaborate (-2) comprising reacting at least one metal hydride with at least one alkyl borate in the presence of at least one Lewis base to generate a Lewis base-borane complex, and reacting the Lewis base-borane complex with at least one metal salt to form a reaction product comprising salts of dodecahydrododecaborate (-2), and optionally recycling alkyl borate from the reaction by-products wherein reactants and reaction products of the process are substantially free of diboranes.

2. A process of claim 1 wherein the at least one metal hydride comprises at least one member selected from the group consisting of alkali metal hydrides, alkaline earth metal hydrides, aluminum hydride and combinations thereof.

3. A process of claim 1 wherein the Lewis base comprises an amine.

4. A process of 1 wherein the Lewis base comprises triethylamine.

5. A process of claim 1 wherein sodium hydride and a trimethylborate are reacted in the presence of at least one inert liquid dispersant.

6. A process of claim 5, wherein the inert liquid dispersant comprises at least one member selected from the group consisting of diethyl ether, tetrahydrofuran, 1,2-dimethoxyethane, and diglyme.

7. A process of claim 1 wherein Lewis base-borane complex is separated from sodium tetramethoxyborate by distillation.

8. A process of claim 1 wherein the reaction byproduct comprises sodium tetramethoxyborate and is separated by filtration.

9. A process of claim 6 wherein a mixture of reaction by-products comprising at least one of sodium tetramethoxyborate and Lewis base-borane complex, is treated with carbon dioxide to recycle trimethylborate.

10. A process of claim 1 wherein the reaction by-product comprises sodium tetramethoxyborate which is mixed with at least one inert liquid dispersant and treated with at least one acid to release trimethylborate, which is separated from the sodium salt of the acid and recycled.

11. A process of claim 10 wherein the inert liquid dispersant comprises trimethylborate, B(OMe)3.

12. A process of claim 11 wherein liquid dispersant comprises a combination of methanol and trimethylborate, B(OMe)3.

13. A process of claim 10 wherein the at least one acid comprises concentrated sulfuric acid.

14. A process of claim 1 wherein the reaction product comprises sodium tetramethoxyborate which is heated to a temperature from about 150 to about 300 C to produce sodium methoxide and trimethylborate, which is recycled.

15. A process of claim 14 wherein sodium tetramethoxyborate is heated in the presence of at least one inert dispersant.

16. A process of claim 15, wherein inert dispersant comprises at least one aliphatic hydrocarbon.

17. A process of claim 1 wherein the reaction product comprises sodium tetramethoxyborate which is treated in an inert dispersant with NaH at a temperature from about 100 to about 300 C to form sodium tetrahydroborate, NaBH4.

18. A process for producing salts of dodecahydrododecaborate (-2) comprising reacting at least one metal hydride with at least one alkyl borate in the presence of at least one Lewis base to generate a Lewis base-borane complex, and reacting the Lewis base-borane complex with at least one metal salt to form a reaction product comprising salts of dodecahydrododecaborate (-2), and wherein the reaction product further comprises sodium tetramethoxyborate which is further reacted to produce sodium methoxide and trimethylborate wherein the reactants and reaction products of the process are substantially free of diboranes.

19. A process for producing salts of dodecahydrododecaborate (-2) comprising reacting at least one hydride with at least one alkylborate in the presence of at least one Lewis base to obtain a Lewis base-borane complex, and contacting the Lewis base-borane complex with sodium borohydride to obtain salts of dodecahydrododecaborate (-2) wherein said dodecahydroborate (-2) comprises $Na_2B_{12}H_{12}$ wherein reactants and products of the process are substantially free of diboranes.

20. The process of claim 19 wherein the at least one alkylborate comprises trimethylborate.

21. The process of claim 19 wherein the at least one hydride comprises sodium hydride.

22. The process of claim 20 further comprising contacting the at least one hydride with the at least one alkylborate in the presence of triethylamine and at least one Lewis base.

23. A process for producing salts of dodecahydrododecaborate (-2) comprising reacting at least one metal hydride with at least one alkyl borate in the presence of at least one Lewis base to form a reaction product comprising salts of dodecahydrododecaborate (-2), and recovering the dodecahydrododecaborate (-2) wherein reactants and reaction products of the process are substantially free of diboranes.

24. The method of claim 23 further comprising recycling alkyl borate.

25. A process for producing salts of dodecahydrododecaborate comprising:
reacting sodium hydride with trimethyl borate in the presence of at least one amine to form a borane triethylamine complex,
reacting the borane triethylamine complex with at least one metal salt to form a salt of dodecahydrododecaborate,
recycling trimethylborate;
and wherein reactants and products of the process are substantially free of diboranes.

26. The process of claim 25 wherein said at least one amine comprises triethylamine.

27. The process of claim 1 wherein said Lewis base comprises an amine containing at least one aryl or aralkyl group.

28. The process of claim 27 wherein said amine comprises diethylaniline.

29. The process of claim 1 wherein said Lewis base comprises an amine containing branched alkyl groups or cyclic alkyls.

30. The process of claim 29 wherein said amine comprises N-ethyl-morpholine.

31. The process of claim 1 wherein said process comprises reacting amine-borane complex with at least one metal salt to form a reaction product comprising salts of dodecahydrododecaborate (-2).

32. The process of claim 31 wherein said amine comprises an amine containing at least member selected from group consisting of aryl, aralkyl, cyclic hydrocarbon or branched alkyl.

* * * * *